United States Patent
Juneau et al.

(10) Patent No.: US 7,217,335 B2
(45) Date of Patent: *May 15, 2007

(54) METHOD OF MANUFACTURING A SOFT HEARING AID

(75) Inventors: Roger P. Juneau, Destrehan, LA (US); Lynn P. Creel, Kenner, LA (US); Edward J. Desporte, Covington, LA (US); Michael Major, Mandeville, LA (US); Gregory R. Siegle, Kenner, LA (US); Kelly M. Kinler, Luling, LA (US)

(73) Assignee: Softear Technologies, L.L.C., Harahan, LA (US)

( * ) Notice: Subject to any disclaimer, the term of this patent is extended or adjusted under 35 U.S.C. 154(b) by 226 days.

This patent is subject to a terminal disclaimer.

(21) Appl. No.: 10/784,534

(22) Filed: Feb. 23, 2004

(65) Prior Publication Data
US 2004/0252854 A1  Dec. 16, 2004

Related U.S. Application Data

(60) Continuation-in-part of application No. 09/855,095, filed on May 14, 2001, now Pat. No. 6,695,943, which is a continuation-in-part of application No. 09/311,156, filed on May 13, 1999, now Pat. No. 6,354,990, which is a continuation-in-part of application No. 09/181,539, filed on Oct. 28, 1998, now Pat. No. 6,728,383, and a continuation-in-part of application No. 09/181,540, filed on Oct. 28, 1998, now Pat. No. 6,432,247, and a continuation-in-part of application (Continued)

(51) Int. Cl.
*B29C 33/40* (2006.01)
*B29C 33/42* (2006.01)

(52) U.S. Cl. .................. 156/245; 156/329; 156/344; 264/134; 264/135; 264/222; 264/225; 264/226; 264/227; 264/272.11; 264/272.14; 264/272.15

(58) Field of Classification Search .............. 264/222, 264/134, 135, 225–226, 227, 292.11, 292.14, 264/292.15; 156/245, 329, 344
See application file for complete search history.

(56) References Cited

U.S. PATENT DOCUMENTS 3,345,737 A   10/1967   Gordon
(Continued)

FOREIGN PATENT DOCUMENTS

JP          61-238198         10/1986
(Continued)

OTHER PUBLICATIONS

Wayne J. Staab, PhD, and Barry Finlay, A Fitting Rationale For Deep Fitting Canal Hearing Instruments, 1991, pp. 7-10 and 48, vol. 42, No. 1, Hearing Instruments, U.S.
Robert J. Oliveira, The Active Earcanal, 1997, pp. 401-410, vol. 8, No. 6, Journal of the American Academ of Audiology, U.S.

*Primary Examiner*—Stefan Staicovici
(74) *Attorney, Agent, or Firm*—Garvey, Smith, Nehrbass & North L.L.C.; Charles C. Garvey, Jr.; Seth M. Nehrbass

(57) ABSTRACT

A method of manufacturing a hearing aid preferably includes the steps of: placing a moldable material in the ear canal of a patient to cast a form; using the form to form a hollow shell with an outer surface that approximates the shape of the patient's ear canal, the shell being of a soft polymeric material providing a mounting member; mounting electronic hearing aid components to the mounting member; joining the mounting member to the hollow shell to define a mold cavity; and filling the shell with a soft polymeric material that substantially encapsulates at least one of the electronic components and bonds to the mounting member, wherein the combination of shell, electronic components and soft polymeric material define a soft structure that is compliant to ear canal movement during use.

52 Claims, 11 Drawing Sheets

Related U.S. Application Data

No. 09/181,541, filed on Oct. 28, 1998, now Pat. No. 6,438,244, and a continuation-in-part of application No. 09/181,842, filed on Oct. 28, 1998, now Pat. No.6,254,526, and a continuation-in-part of application No. 09/181,843, filed on Oct. 28, 1998, now Pat. No. 6,434,248, and a continuation-in-part of application No. 09/181,844, filed on Oct. 28, 1998, now Pat. No. 6,228,020, and a continuation-in-part of application No. 09/181,845, filed on Oct. 28, 1998, now Pat. No. 6,473,512, which is a continuation-in-part of application No. 09/084,864, filed on May 26, 1998, now Pat. No. 6,022,311, application No. 10/784,534, which is a continuation-in-part of application No. 10/097,540, filed on Mar. 11, 2002, now Pat. No. 6,761,789, which is a division of application No. 09/311,156, filed on May 13, 1999, now Pat. No. 6,354,990.

U.S. PATENT DOCUMENTS

| Patent No. | | Date | Inventor | |
|---|---|---|---|---|
| 3,470,328 A | * | 9/1969 | Daniels | 381/322 |
| 3,527,901 A | | 9/1970 | Geib | |
| 4,051,330 A | | 9/1977 | Cole | |
| 4,375,016 A | | 2/1983 | Harada | |
| 4,569,812 A | | 2/1986 | Werwath et al. | |
| 4,607,720 A | | 8/1986 | Hardt | |
| 4,706,778 A | | 11/1987 | Topholm | |
| 4,716,985 A | | 1/1988 | Haertl | |
| 4,739,512 A | | 4/1988 | Hartl | |
| 4,811,402 A | | 3/1989 | Ward | |
| 4,834,927 A | | 5/1989 | Birkholz et al. | |
| RE33,017 E | | 8/1989 | Bellafiore | |
| 4,860,362 A | | 8/1989 | Tweedle | |
| 4,870,688 A | | 9/1989 | Voroba et al. | |
| 4,871,502 A | | 10/1989 | Lebisch et al. | |
| 4,880,076 A | | 11/1989 | Ahlberg et al. | |
| 4,937,876 A | | 6/1990 | Biermans | |
| 5,002,151 A | | 3/1991 | Oliveira et al. | |
| 5,068,902 A | | 11/1991 | Ward | |
| 5,185,802 A | | 2/1993 | Stanton | |
| 5,201,007 A | | 4/1993 | Ward et al. | |
| 5,259,032 A | | 11/1993 | Perkins et al. | |
| 5,319,163 A | | 6/1994 | Scott | |
| 5,321,757 A | * | 6/1994 | Woodfill, Jr. | 381/312 |
| 5,357,576 A | * | 10/1994 | Arndt | 381/328 |
| 5,357,786 A | | 10/1994 | Lung et al. | |
| 5,430,801 A | | 7/1995 | Hill | |
| 5,500,902 A | | 3/1996 | Stockham, Jr. et al. | |
| 5,530,763 A | | 6/1996 | Aebi et al. | |
| 5,572,594 A | * | 11/1996 | Devoe et al. | 381/328 |
| 5,659,621 A | | 8/1997 | Newton | |
| 5,748,743 A | | 5/1998 | Weeks | |
| 5,917,918 A | | 6/1999 | Callahan | |
| 5,999,632 A | | 12/1999 | Leysieffer et al. | |
| 6,022,311 A | | 2/2000 | Juneau et al. | |
| 6,052,473 A | | 4/2000 | Clavadetscher et al. | |
| 6,228,020 B1 | | 5/2001 | Juneau et al. | |
| 6,249,587 B1 | | 6/2001 | Clavadetscher et al. | |
| 6,432,247 B1 | | 8/2002 | Juneau et al. | |

FOREIGN PATENT DOCUMENTS

| | | |
|---|---|---|
| WO | WO 93/25053 | 12/1993 |
| WO | WO 99/31934 | 6/1999 |
| WO | WO 99/31935 | 6/1999 |

* cited by examiner

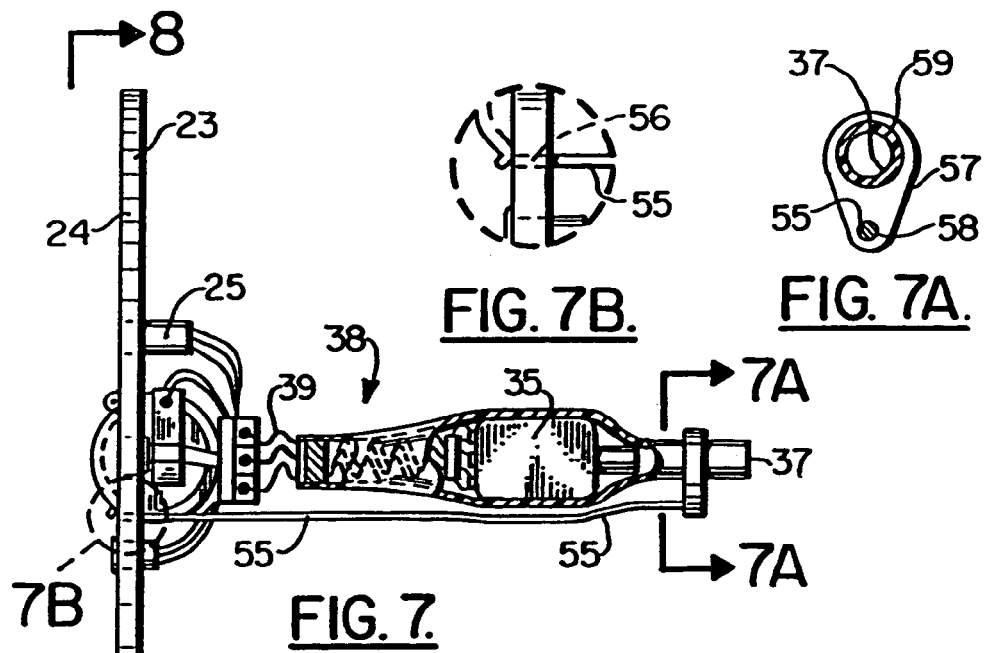
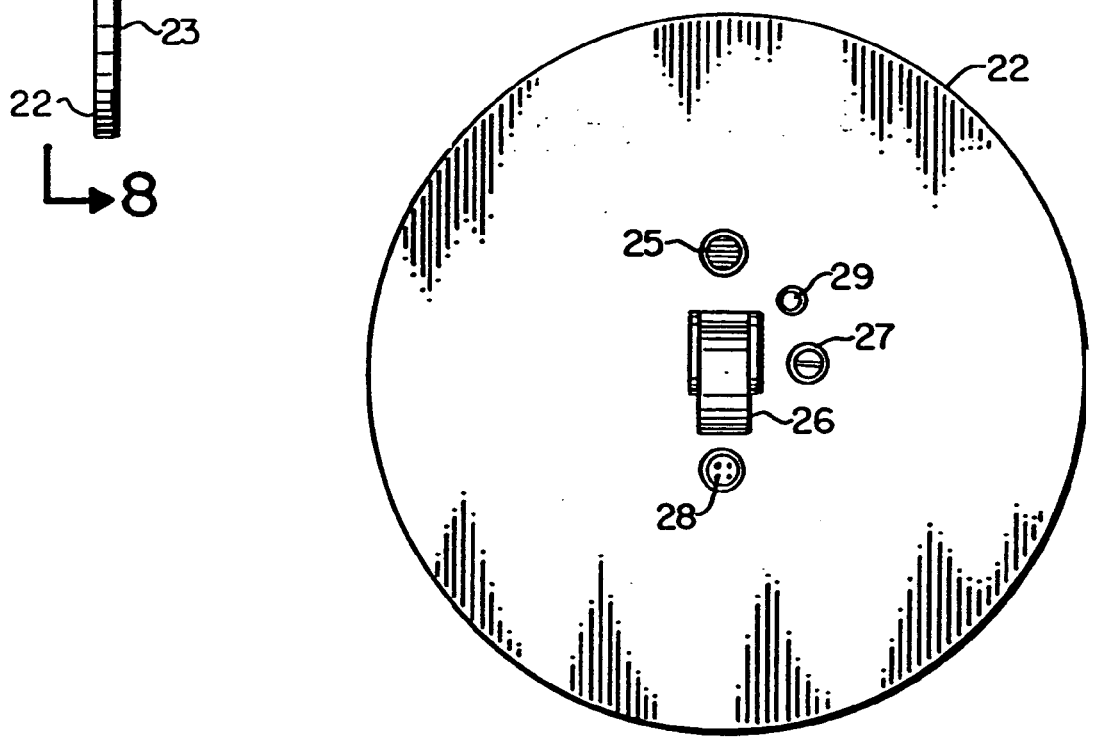

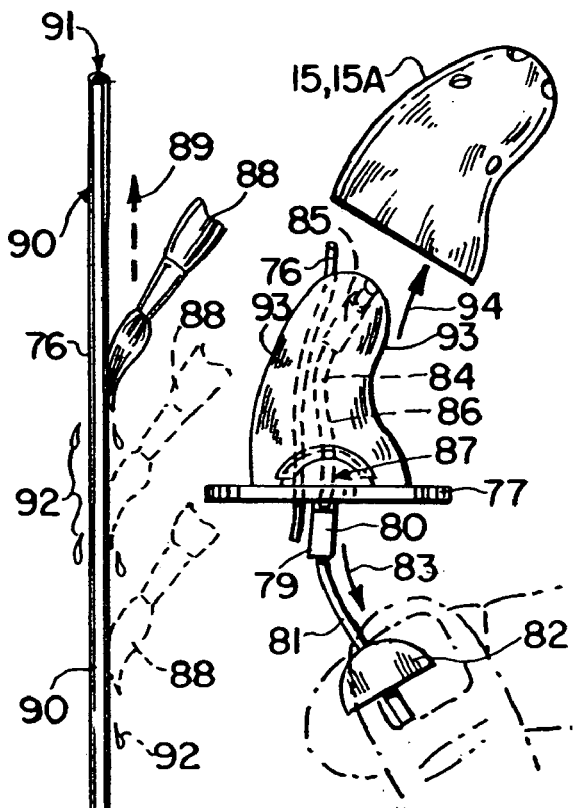
FIG. 27.
FIG. 28.
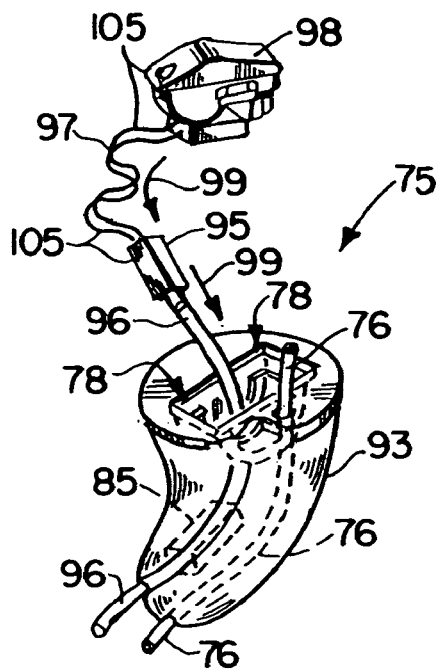
FIG. 29.
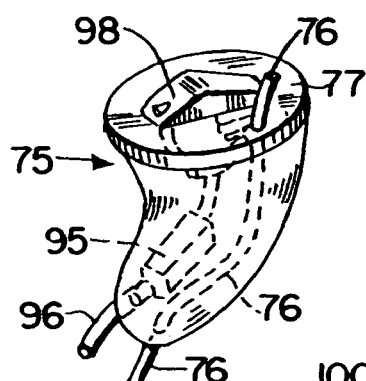
FIG. 30.
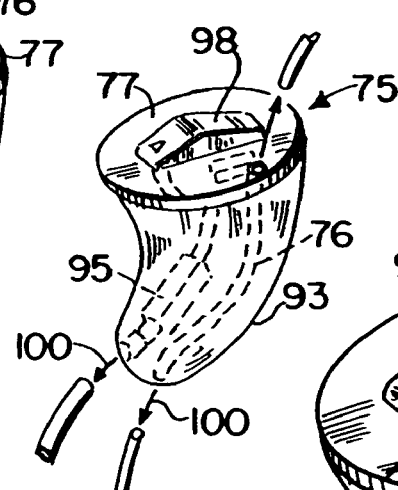
FIG. 31.
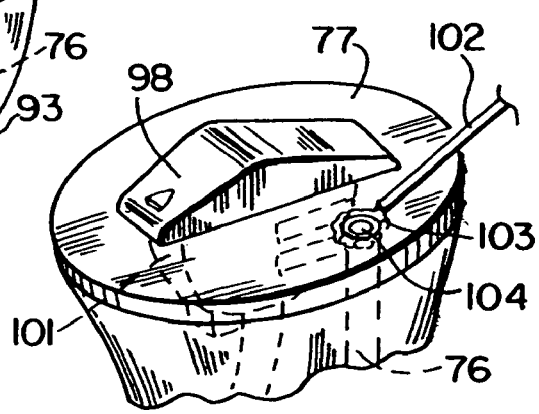
FIG. 32.

METHOD OF MANUFACTURING A SOFT HEARING AID

CROSS-REFERENCE TO RELATED APPLICATIONS

This application is a continuation-in-part of U.S. patent application Ser. No. 09/855,095, filed 14 May 2001 (now U.S. Pat. No. 6,695,943), which is a continuation-in-part of U.S. patent application Ser. No. 09/311,156, filed 13 May 1999 (now U.S. Pat. No. 6,354,990), which is a continuation-in-part of U.S. patent application Ser. No. 09/181,539 now U.S. Pat. No. 6,728,383, Ser. No. 09/181,540 (now U.S. Pat. No. 6,432,247), Ser. No. 09/181,541 (now U.S. Pat. No. 6,438,244), Ser. No. 09/181,842 (now U.S. Pat. No. 6,254,526), Ser. No. 09/181,843 (now U.S. Pat. No. 6,434,248), Ser. No. 09/181,844 (now U.S. Pat. No. 6,228,020) and Ser. No. 09/181,845 (now U.S. Pat. No. 6,473,512), all filed 28 Oct. 1998, which are continuations-in-part of U.S. patent application Ser. No. 09/084,864, filed 26 May 1998 (now U.S. Pat. No. 6,022,311). Each of these patent applications and patents are incorporated herein by reference. Priority of each of these patent applications is hereby claimed.

This is also a continuation-in-part of U.S. patent application Ser. No. 10/097,540, filed 11 Mar. 2002, (now U.S. Pat. No. 6,761,789), which is a divisional of U.S. patent application Ser. No. 09/311,156 filed May 13, 1999 (now U.S. Pat. No. 6,354,990).

Priority of U.S. Provisional Patent Application Ser. No. 60/456,057, filed 20 Mar. 2003, incorporated herein by reference, is hereby claimed.

Priority of U.S. Provisional Patent Application Ser. No. 60/450,898, filed 28 Feb. 2003, incorporated herein by reference, is hereby claimed.

Priority of U.S. Provisional Patent Application Ser. No. 60/203,983, filed 12 May 2000, incorporated herein by reference, is hereby claimed.

Priority of U.S. Provisional Patent Application Ser. No. 60/068,036, filed 18 Dec. 1997, incorporated herein by reference, is hereby claimed.

STATEMENT REGARDING FEDERALLY SPONSORED RESEARCH OR DEVELOPMENT

Not applicable

REFERENCE TO A "MICROFICHE APPENDIX"

Not applicable

BACKGROUND OF THE INVENTION

1. Field of the Invention

The present invention relates to hearing aids and more particularly to an improved hearing aid and its method of manufacture. More particularly, the present invention provides an improved method for constructing a hearing aid combining a mounting member (for example, a receptacle or face plate) with a soft polymeric body that is joined to the mounting member and which encapsulates one or more of the electronic hearing aid components of the apparatus, the soft polymeric body being sized and shaped to conform to the user's ear canal during use. In one form, a soft polymeric material is used as the face plate.

2. General Background of the Invention

The hearing industry has realized major strides in the development of high-fidelity, high-performance products, the most recent of which is digital signal processing technology. Hearing care professionals expected those advancements to solve the shortcomings of traditional amplification, and to push the market forward. Those expectations have not been fully realized. While these developments have solved many of the problems associated with traditional electronic design and steadily gained market share, they have not fostered overall market growth.

The issues of early acoustic feedback, less than optimum fidelity and intermodulation of the frequency response cannot be completely resolved by electronic manipulation of the signal by either analog or digital means.

Historically, custom-molded ear worn hearing instruments have been limited to an "acrylic pour" process as the means of the construction. With the advent of miniaturization and technological advancement of computer chip programming, the ear-worn instruments have become smaller and are positioned into the bony portion of the ear canal, commonly referred to as "deep insertion technology."

Developments outside the hearing industry have culminated in a new level of micro-miniaturization of electronic components for industry applications. Consequently, advanced signal processing can be housed in less space than was required for traditional electro-acoustic components.

With the development of programmable hearing aids, using either analog or digital signal processing, custom electronic design has shifted from the manufacturing level to the clinical level. The clinician can now customize the electro-acoustic response via software. It is no longer necessary for the device to be returned to the manufacturer for hardware changes to arrive at the desired electro-acoustic response. However, it is still often necessary to return the device for shell modifications.

In direct contrast to electronic advances within the industry, little or no advancement has been realized in custom prosthetic design. Since the late 1960's, when the custom in-the-ear hearing aid was developed, materials and construction techniques remained virtually unchanged. These materials and techniques were adopted from the dental industry, whereby the customized housing-commonly called a "shell" was constructed using acrylic of 90 point Durometer Hardness Shore D. This construction process provided the structure and the strength of material necessary to protect the electronics.

At the time the acrylic shell was developed, hearing instruments were worn in the relatively forgiving cartilaginous portion of the ear canal. Micro-miniaturization of electronic components, combined with increased consumer demand for a cosmetically acceptable device, has shifted the placement of the hearing aid toward the bony portion of the ear canal.

The bony portion of the canal is extremely sensitive and intolerant of an acrylic shell when that shell is over sized due to standard waxing procedures or is in contact with the canal wall beyond the second anatomical bend. Rigid acrylic that does not compress must pivot in reaction to jaw or head movement, thereby changing the direction of the receiver yielding a distorted acoustic response. In addition, the pivot action causes displacement of the device resulting in unwanted acoustic feedback. This problem has necessitated countless shell modifications, thereby compromising the precision approach of the original dental technology. Many such devices require some modification by the manufacturer. Most manufacturers can expect a high percentage of returns for modification or repair within the first year. Consequently, CIC (completely in canal) shell design has been reduced to more of a craft than a science. Although the recent introduction of the ultra-violet curing process has produced a stronger, thinner shell, the overall Shore Hardness remained unchanged.

The current trend for custom hearing aid placement is to position the instrument toward the bony portion of the ear canal. The ear canal can be defined as the area extending from the concha to the tympanic membrane. It is important to note that the structure of this canal consists of elastic cartilage laterally, and porous bone medially. The cartilaginous portion constitutes the outer one third of the ear canal. The medial two-thirds of the ear canal is osseous or bony. The skin of the osseous canal, measuring only about 0.2 mm in thickness, is much thinner than that of the cartilaginous canal, which is 0.5 to 1 mm in thickness. The difference in thickness directly corresponds to the presence of apocrine (ceruminous) and sebaceous glands found only in the fibro-cartilaginous area of the canal. Thus, this thin-skinned thinly-lined area of the bony canal is extremely sensitive to any hard foreign body, such as an acrylic hearing instrument.

Exacerbating the issue of placement of a hard foreign body into the osseous area of the ear canal is the ear canal's dynamic nature. It is geometrically altered by temporomandibular joint action and by changes in head position. This causes elliptical elongation (widening) of the ear canal. These alterations in canal shape vary widely from person to person. Canal motion makes it very difficult to achieve a comfortable, true acoustic seal with hard acrylic material. When the instrument is displaced by mandibular motion, a leakage or "slit leak" creates an open loop between the receiver and the microphone and relates directly to an electroacoustic distortion commonly known as feedback. Peripheral acoustic leakage is a complex resonator made up of many transient resonant cavities. These cavities are transient because they change with jaw motion as a function of time, resulting in impedance changes in the ear canal. These transients compromise the electroacoustic performance.

The properties of hard acrylic have limitations that require modification to the hard shell exterior to accommodate anatomical variants and the dynamic nature of the ear canal. The shell must be buffed and polished until comfort is acceptable. The peripheral acoustic leakage caused by these modifications results in acoustic feedback before sufficient amplification can be attained.

Hollow shells used in today's hearing aid designs create internal or mechanical feedback pathways unique to each device. The resulting feedback requires electronic modifications to "tweak" the product to a compromised performance or a "pseudo-perfection". With the industry's efforts to facilitate the fine-tuning of hearing instruments for desired acoustic performance, programmable devices were developed. The intent was to reduce the degree of compromise, but by their improved frequency spectrum the incidence of feedback was heightened. As a result, the industry still falls well short of an audiological optimum.

A few manufacturers have attempted all-soft, hollow shells as alternatives to acrylic, hollow shells. Unfortunately, soft vinyl materials shrink, discolor, and harden after a relatively short period of wear. Polyurethane has proven to provide a better acoustic seal than polyvinyl, but has an even shorter wear life (approximately three months). Silicones have a long wear life but are difficult to bond with plastics such as acrylic, a necessary process for the construction of custom hearing instruments. To date, acrylic has proven to be the only material with long term structural integrity. The fact remains, however, that the entire ear is a dynamic acoustic environment and is ill-served by a rigid material such as acrylic. Also, the acrylic hearing aids typically need to be returned to the manufacturer for major shell modifications.

The following references are all incorporated herein by reference:

U.S. Pat. Nos.: 4,051,330; 4,375,016; 4,607,720; 4,716,985; 4,811,402; 4,870,688; 4,880,076; 4,937,876; 5,002,151; 5,068,902; 5,185,802; 5,201,007; 5,259,032; 5,530,763; 5,430,801; 5,500,902; and 5,659,621.

A Japanese reference that discusses a hearing aid that features a thin wall soft shell is the Takanishi patent application number 1989-238198.

Also of interest and incorporated herein by reference are published Japanese patent application no. JA61-238198, the articles from December 1997 Journal of American Academy of Audiology, and Staab, Wayne J. and Barry Finlay, "A fitting rationale for deep fitting canal hearing instruments", Hearing Instruments, Vol. 42, No. 1, 1991, pp. 7–10, 48.

BRIEF SUMMARY OF THE INVENTION

The present invention provides a method and material for the construction of a soft hearing instrument that is solid (i.e. eliminates void spaces). This instrument includes a soft body portion that is truly soft, comprising an elastomer of about 3 to 55 durometer Shore A and preferably 10–35 durometer Shore A. This product is unique in that it is solid, with the electronic components actually encapsulated or embedded within the soft fill material. The fill material can be a Dow Corning® MDX-4-4210 silicone or a silicone polymer distributed by Factor II, Inc. of Lakeside, Ariz., designated as product name 588A, 588B, 588V.

The present invention provides a method that can replace traditional acrylic shell construction. Unlike the shell construction process, the ear impression is not modified, built up, or waxed. With the elimination of these steps, a more faithful reproduction of the ear impression is accomplished. With the present invention, the manufacturer should be able to produce a hearing aid body which will not need to be returned as frequently for modification as with present hard acrylic hearing aid bodies.

The apparatus of the present invention is virtually impervious to the discoloration, cracking, and hardening experienced with polyvinyls and polyurethanes.

The hearing aid of the present invention provides a greater range of gain before feedback occurs.

The outer surface of the body of the present invention is preferably non-absorbent and virtually impervious to cerumen.

As used herein, "in the ear hearing aids" includes all hearing aids which have all of the electronics positioned in the ear, and thus includes hearing aid styles ranging from full concha to CIC (completely in the canal) hearing aid styles. An embodiment of the present invention shown in the drawings is a CIC hearing aid style.

BRIEF DESCRIPTION OF THE DRAWINGS

For a further understanding of the nature, objects, and advantages of the present invention, reference should be had to the following detailed description, read in conjunction with the following drawings, wherein like reference numerals denote like elements and wherein:

FIG. 7 is a partial elevational view of an embodiment of the apparatus of the present invention illustrating the mounting member and the plurality of the electronic hearing aid components;

FIG. 7A is a cross-sectional view taken along the line 7A—7A in FIG. 7;

FIG. 7B is a partial view showing the portion indicated in FIG. 7 as 7B;

FIG. 8 is a elevational view of the lateral side of the mounting member taken along lines 8—8 of FIG. 7;

FIG. 27 is a partial perspective view showing a second alternate embodiment of the method of the present invention, showing the coating of the vent tube;

FIG. 28 is a partial perspective view showing a second alternate embodiment of the method of the present invention, showing removal of the mold to provide a soft solid body with contained vent tube and insert;

FIG. 29 is a partial perspective view showing a second alternate embodiment of the method of the present invention, illustrating an insertion of the hearing aid component assembly into the void space that was formed by removal of the insert;

FIG. 30 is a perspective view that illustrates the second alternate embodiment of the method and apparatus of the present invention;

FIG. 31 is a perspective view illustrating the second alternate embodiment of the method and apparatus of the present invention; and FIG. 32 is a perspective view illustrating the second alternate embodiment of the method and apparatus of the present invention.

DETAILED DESCRIPTION OF THE INVENTION

Figure 1:
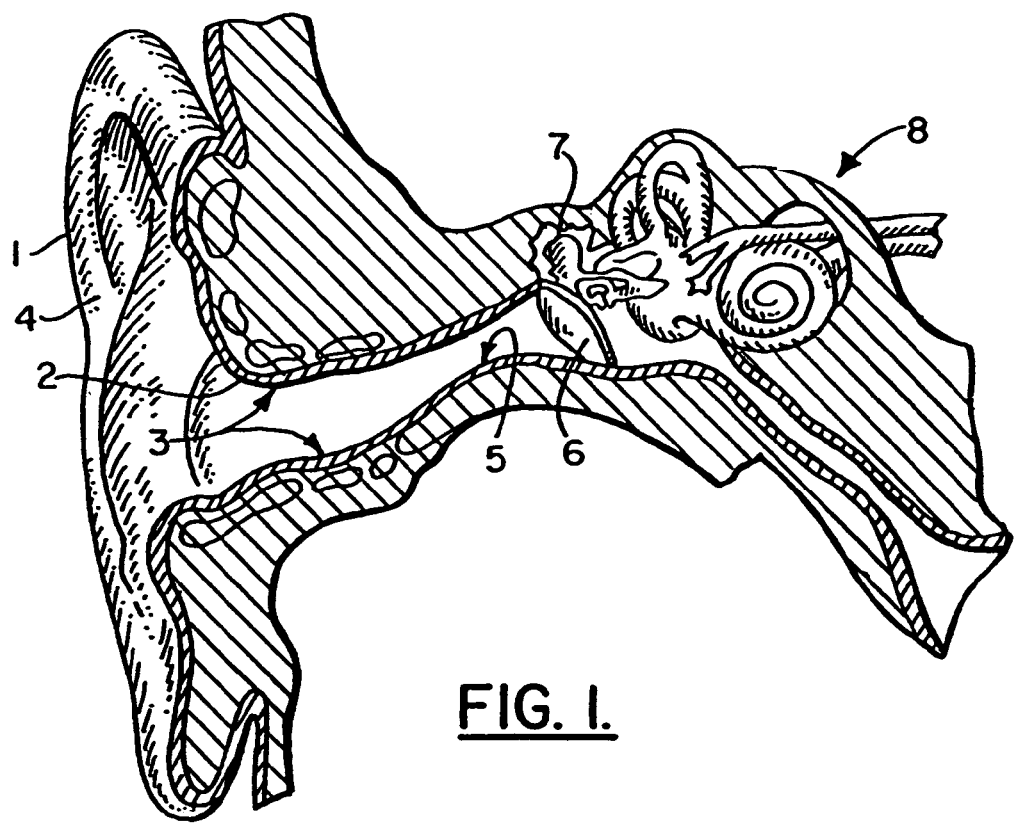
FIG. 1 is a sectional elevational view of a user's hearing area to show the anatomy thereof.
Figure 2:
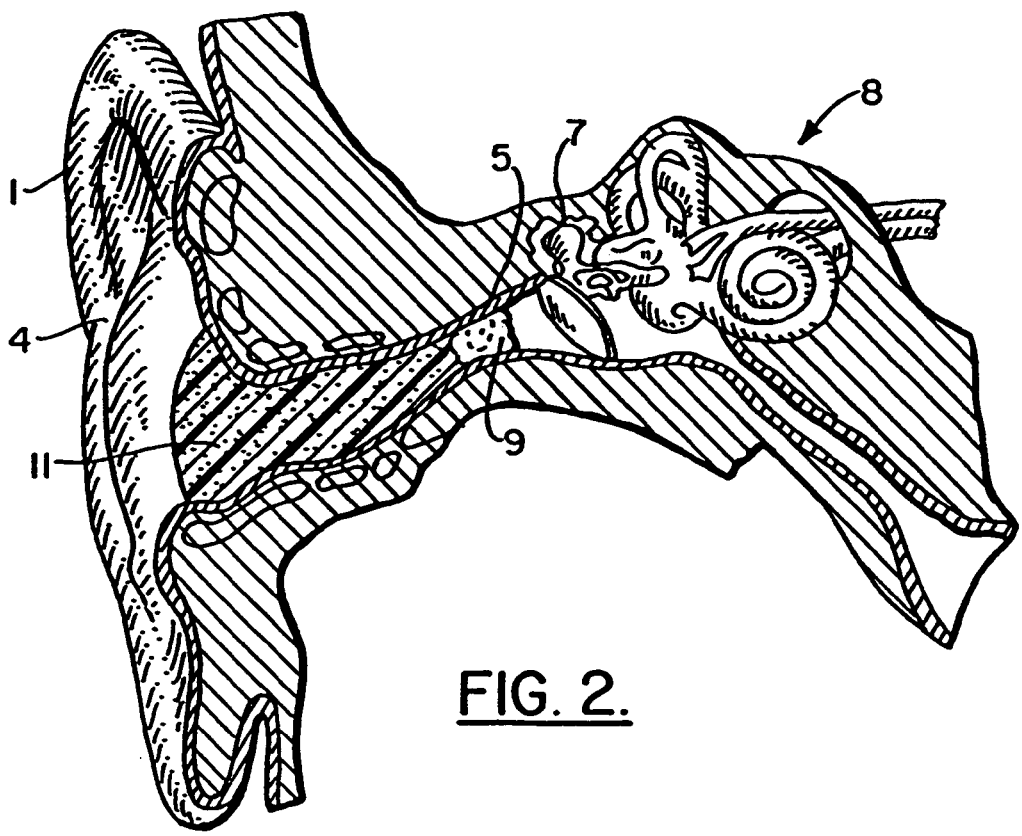
FIG. 2 is a sectional elevational view of a user's ear canal showing placement of a dam and mold material as part of the method of the present invention.

FIGS. 1 and 2 show a user's ear 1 and anatomical parts of the ear. In FIG. 1 there can be seen the external auditory canal 2, ear canal wall 3, auricle 4, isthmus 5, tympanic membrane 6, middle ear 7 and inner ear 8. In FIG. 2 a dam 9 such as a cotton dam or otoblock dam is positioned at the isthmus 5. The dam 9 is used as a first step of an embodiment of the method of the present invention wherein a form portion 11 or impression material is formed of silicone, methylmethacrylate or alginate. The form 11 is formed in between dam 9 and auricle 4 as shown in FIG. 2.

During the method step of making form 11, the form 11 conforms to all of the curvatures of the ear canal 3 so that an accurate form 11 is provided for making a female mold.

Figure 3:
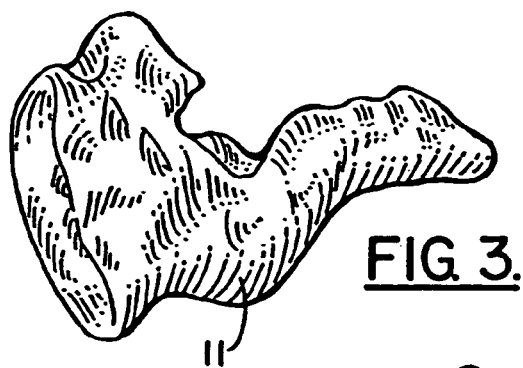
FIG. 3 is a perspective view of the form portion used with an embodiment of the method of the present invention.
Figure 4:
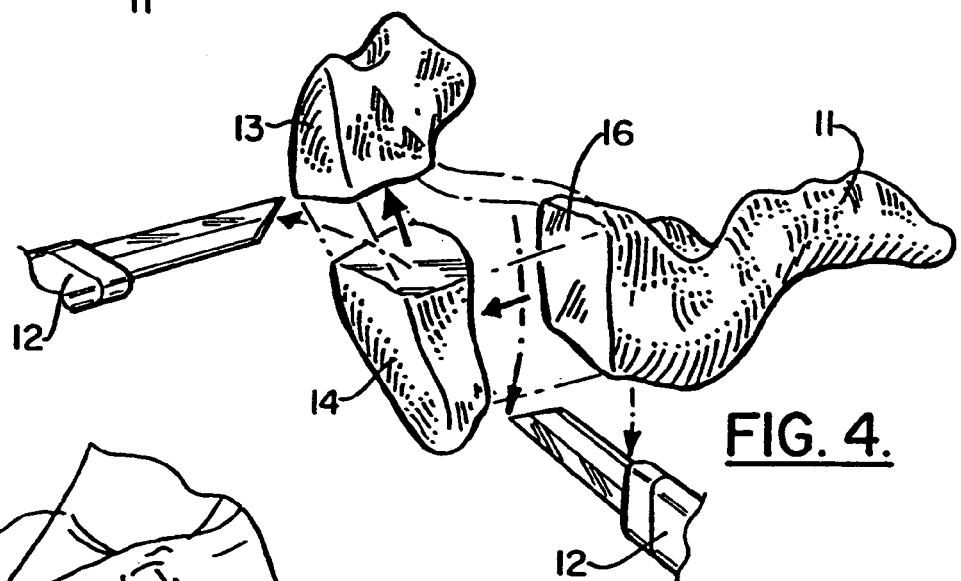
FIG. 4 is a perspective view illustrating shaping of the form as part of the method of the present invention.
Figure 5:
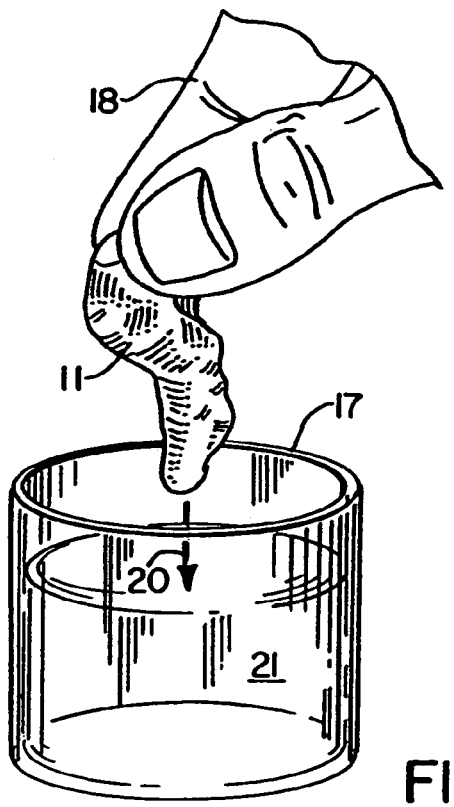
FIG. 5 is a perspective view illustrating a dipping of the form into a vessel carrying material for making the female mold as part of the method of the present invention.

The female mold 15 is shown in FIGS. 6 and 9–12. In FIGS. 3 and 4, the form 11 is shown after being removed from the ear 1 (FIG. 3) and during a cutting of the form 11 using knives 12 to cut excess material that is designated as 13, 14 in FIG. 4. The form 11 is separated from excess material 13 and 14 at sagittal plane 16. After the form 11 is trimmed in FIG. 4, a technician's hand 18 dips the form 11 into vessel 17 as schematically indicated by the arrow 20. The vessel 17 includes a liquid material 21 that cures at room temperature, such as room temperature curing methacrylate (sold by Esschem). A clear material 21 can be used in the method step shown in FIG. 5.

Figure 6:
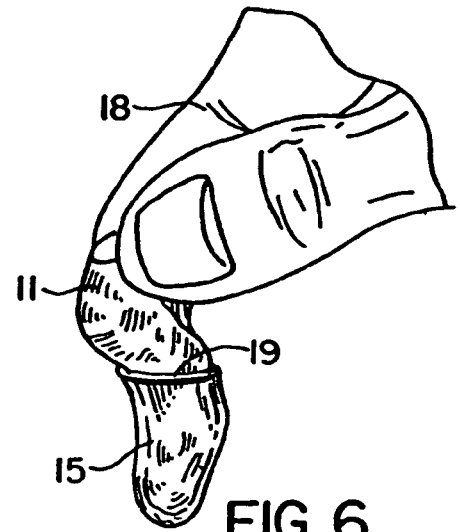
FIG. 6 is a perspective view illustrating a coating of the form with the female mold as part of the method of the present invention.
Figure 9:
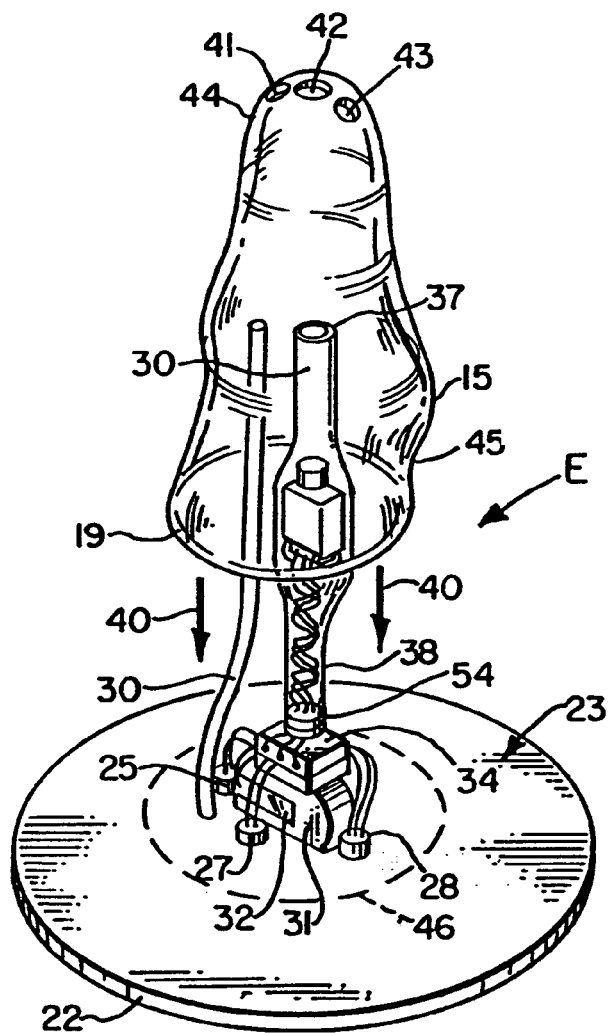
FIG. 9 is a perspective view illustrating the method step of joining the female mold to the mounting member at the medial side thereof.
Figure 10:
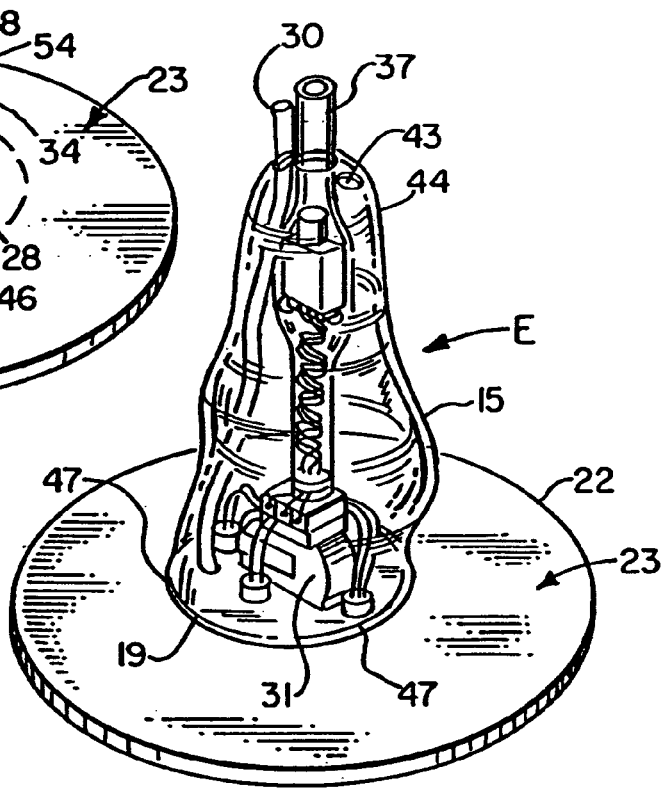
FIG. 10 is a perspective view of an embodiment of the apparatus of the present invention and showing the method of the present invention after the joining of the female mold and mounting member.

In FIG. 6, the technician's hand 18 has removed the form 11 so that a coating of material 21 cures at room temperature (or with an ultraviolet light process) to form female mold 15 on form 11. After it cures, the female mold 15 is removed from form 11 for use as shown in FIGS. 9 and 10 during assembly of the apparatus 10 of the present invention. The mold 15 can be a few millimeters in wall thickness (typically 1–3 mm).

A number of electronic components are mounted to a mounting member 22 prior to use of the female mold 15. Mounting member 22 provides a medial side 23 and lateral side 24. The medial side 23 supports a number of hearing aid electronic components as shown in FIGS. 7, 9, and 10. In FIG. 7, these hearing aid electronic components include commercially available hearing aid components including a microphone 25, volume control, battery, socket or plug 28 for communicating with a computer, chip or micro processor circuit, wiring harness 38, input capacitor, amplifier 34, receiver/speaker 35, and receiver tube 37.

Figure 15:
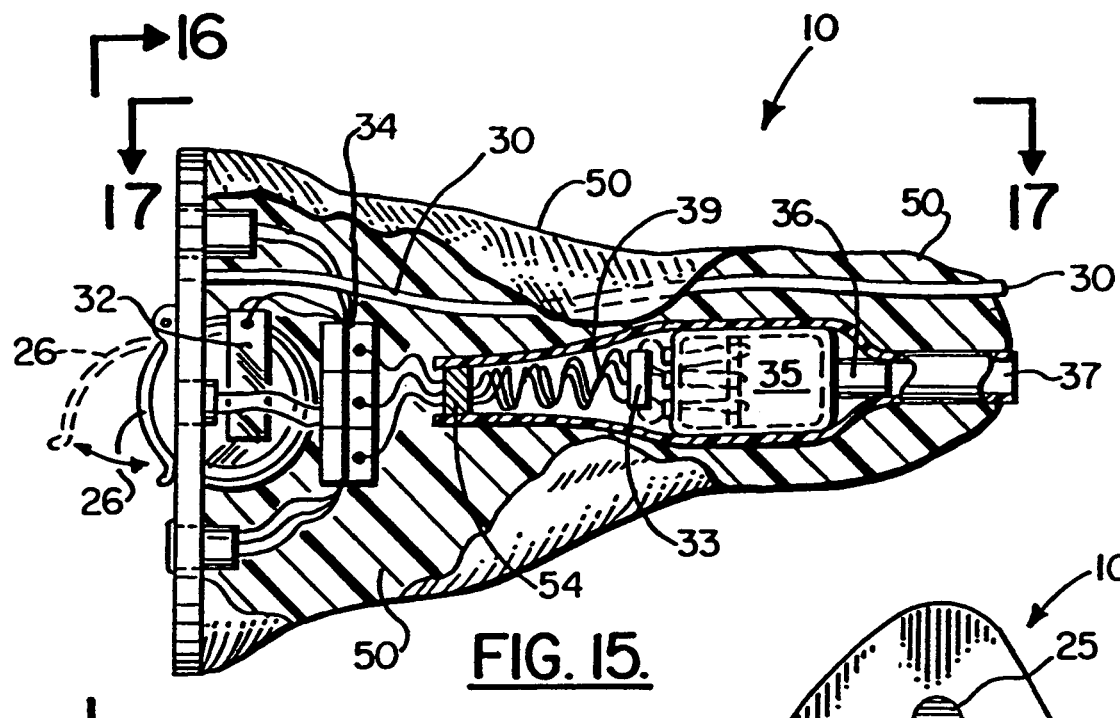
FIG. 15 is an elevational view of an embodiment of the apparatus of the present invention.
Figure 16:
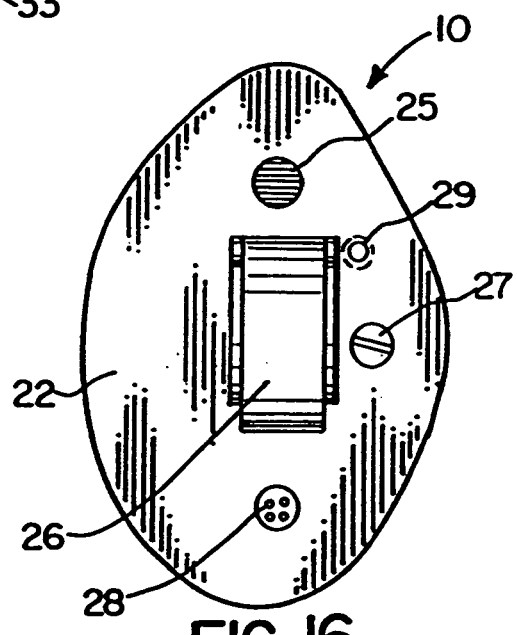
FIG. 16 is an end view of an embodiment of the apparatus of the present invention taken along lines 16—16 of FIG. 15.
Figure 17:
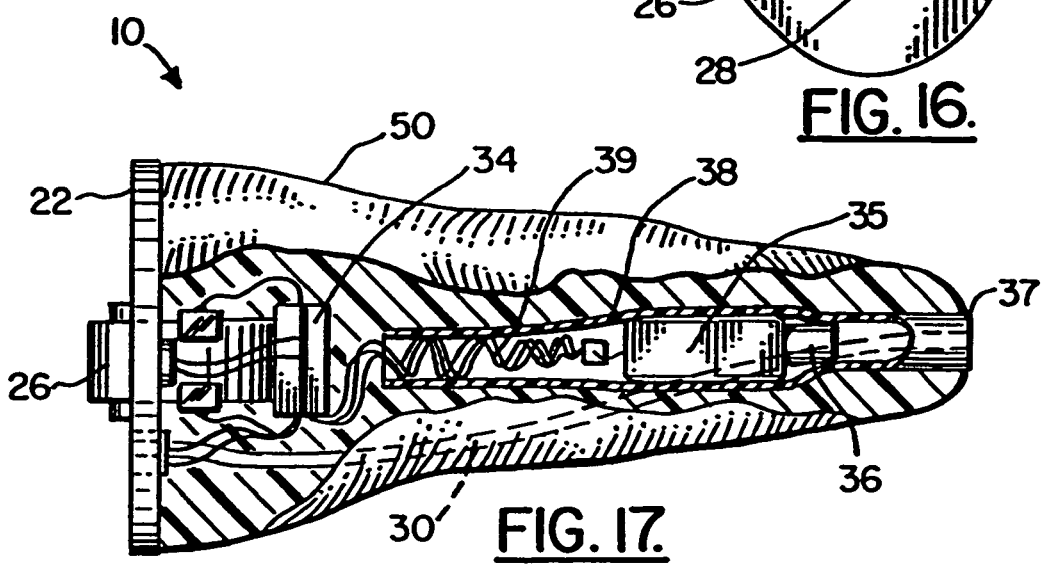
FIG. 17 is a top view of an embodiment of the apparatus of the present invention taken along lines 17—17 of FIG. 15.

In FIG. 8, the lateral side 24 of mounting member 22 shows the microphone 25, battery compartment 26, volume control 27, programming socket 28 for communicating with a computer, silicone plug 54 (see FIG. 9), and vent opening 29 that communicates with vent tube 30 (see FIG. 10). In FIG. 9, battery 31 is shown housed in battery compartment 26. The electronic hearing aid components also include a battery terminal 32, voltage regulating capacitor 33 (see FIG. 15), amplifier/microprocessor 34, receiver 35 having speakerport 36, and receiver tube 37. A wiring harness 38 includes a plurality of wires that connect to various electronic components of the hearing aid device together. The wiring harness 38 includes a length of wires 39 that are arranged in an S or multiple curved pattern as shown in FIG. 7. This "S loop" configuration of wires 39 helps protect the integrity of the electronics when the hearing aid apparatus 10 is flexed as occurs during use because of its soft nature. Further, the S-loop wires 39 are preferably a 44 gauge five strand Litz wire (or magnet wire). The length of the S-loop wires 39 is preferably at least 1.5 times the distance between the terminals to the receiver (or microprocessor) 35 and the amplifier 34 terminals. These "S-Loop" wires 39 prevent excess tension or compression from being transmitted to the electronics during use (e.g. flexing, elongation, compression of hearing aid 10).

Vent tube 30 is anchored to the mounting member 22 and preferably also to one of the electronic components at a position spaced away from the mounting member 22. Vent tube 30 acts as a tensile load carrying member that carries tension so that the wiring harness 38 is substantially free of a tensile load that could damage the wiring harness 38. Also, when vent tube 30 is anchored to one of the electronic components (such as receiver 35) at a position spaced away from the mounting member 22, it may provide enough strain relief that it would not be necessary to coil wires 39 as shown (they could be straight instead).

Something else could be used as a load carrying member, in place of vent tube 30 (in which case vent tube 30 would not necessarily be anchored to one of the electronic components (such as receiver 35)) at a position spaced away from the mounting member 22. For example, a monofilament cantilever 55 can be used to carry tension so that tension is not transmitted to wiring harness 38. In FIGS. 7, 7A, and 7B the link 55 is anchored to plate 22 at opening 56. Fastener 57 affixes to receiver tube 37 at large opening 59. Monofilament cantilever 55 attaches to fastener 57 at smaller diameter opening 58. Alternatively, vent tube 30 could be manufactured of a tensile material that carries tensile load. The vent tube 30 would then be anchored to plate 22 and fastener 57 as the tensile member.

The monofilament cantilever 55 provides longitudinal stability to the body. It minimizes longitudinal displacement (stretching as well as compression) and thus acts as a longitudinal stabilizer (a longitudinal load carrying member). As described above the monofilament cantilever 55 can be used as an alternative embodiment.

After the electronic components (sometimes designated generally in the drawings by the letter "E") are assembled to the medial 23 side of mounting member 22, female mold 15 is used to complete the method of construction of the present invention as shown in FIG. 9-13. In FIG. 9, the female mold 15 is placed over the electronic components "E" beginning with the distal end portion of receiver tube 37 and the distal end portion of vent tube 30 as indicated by arrows 40 in FIG. 9. A plurality of three openings 41, 42, 43 are provided at distal end 44 of female mold 15 as shown in FIG. 9. The proximal end 45 of female mold 15 provides an annular edge surface 19 that engages the medial 23 side of mounting member 22 as indicated by the dotted line 46 in FIG. 9.

A joint is formed between annular edge surface 19 of female mold 15 and medial surface 23 of mounting member 22 at a position schematically indicated as dotted line 46 in FIG. 9, using the method of the present invention. The medial surface 23 of mounting member 22 is cleaned with a suitable solvent. Acetone can be used as a solvent in the case of a mounting plate 22 that is made of acrylic. The medial surface 23 of mounting member 22 is then painted with a primer using a swab or brush. The primer is allowed to dry. A bonding agent is then applied to the medial surface 23 of mounting member 22 and allowed to dry. The bonding agent or bonding enhancer can be product A-320 of Factor II, Inc. of Lakeside, Ariz., which is a member of the chemical family "silicone primer".

The female mold 15 is placed against the medial side 23 of mounting member 22. A liquid acrylic is used to form an acrylic seam at the interface of annular edge surface 19 of female mold 15 and the medial side 23 of mounting member 22 (see FIG. 10). As the female mold 15 is assembled to mounting member 22, vent tube 30 passes through opening 41. Receiver tube 37 passes through opening 42. The opening 43 is then used for injection of filler material 50 (e.g. via needle 49) as shown by arrows 51, 52 in FIG. 11. During this process, temporary seal 47 holds the liquid filler material 50 within the interior 53 that is formed by female mold 15 and mounting member 22. The filler material 50 can be a liquid during the injection step of FIG. 11 so that it encapsulates at least the receiver/speaker electronic component 35 and preferably other components as well.

Figure 12:
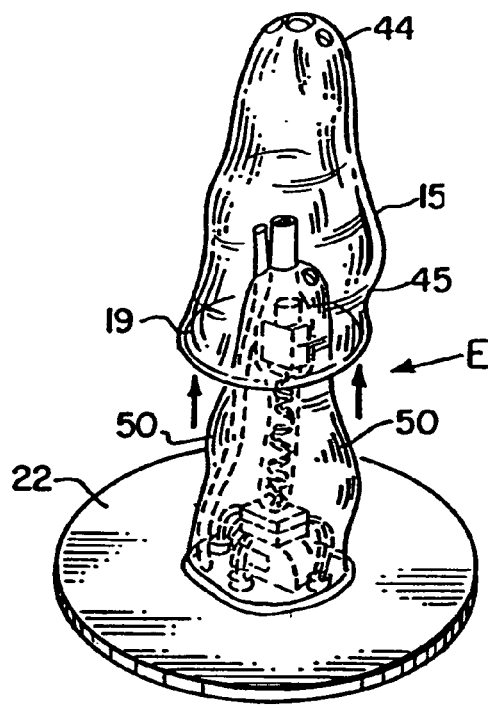
FIG. 12 is a perspective view illustrating removal of the female mold after the filler material has set and encapsulating the electronic hearing aid components.
Figure 14:
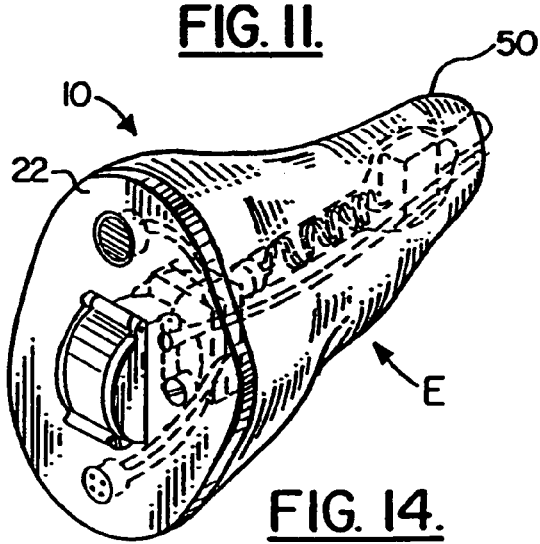
FIG. 14 is a perspective view of an embodiment of the apparatus of the present invention.
Figure 13:
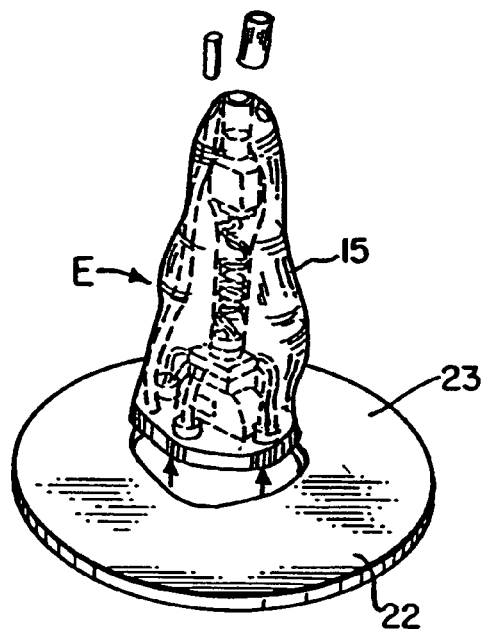
FIG. 13 is a perspective of an embodiment of the apparatus of the present invention and the method of the present invention illustrating removal of excess plate and tube material from the mounting member.

In FIG. 12, the female mold 15 is removed after the material 50 has set. The mounting member 22 (which can be in the form of a circular, generally flat face plate) is then cut at the phantom line 46 that basically tracks the periphery of female mold 15 at annular edge surface 19 at proximal end 45 thereof. This cutting of the unused, unneeded part of mounting member 22 is shown in FIG. 13. FIGS. 14–17 show the completed apparatus 10 of the present invention.

The present invention provides a soft, yet solid hearing aid instrument that will provide a more appropriate environment for both the high fidelity performance of today's advanced circuitry and the dynamic ear canal.

The present invention teaches a soft construction of at least the distal portion of the apparatus 10 so that at least the receiver/speaker is encapsulated with the soft material 50. This construction results in a precise representation of the human ear canal, flex with jaw motion, and cushion for the embedded electronic components "E".

Figure 18:
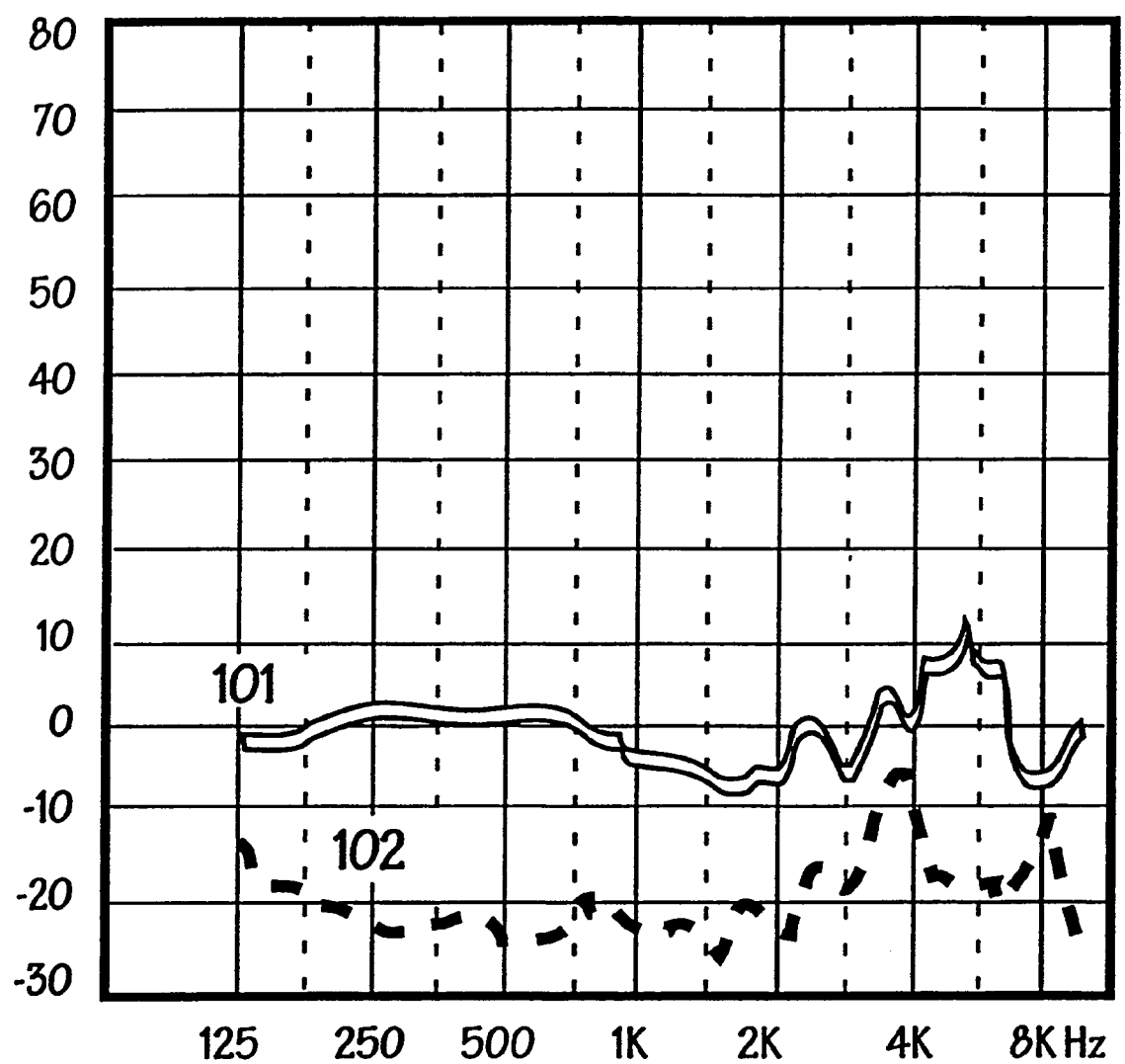
FIG. 18 is a graphical representation of a comparison of real ear occlusion gain for the present invention versus a hard shell, hollow-type instrument.

FIG. 18 demonstrates real ear occlusion gain (REOG) finding obtained from a wearer having a tortuous ear canal. The curve 101 represents the REOG of a hard shell, hollow type hearing aid instrument. The curve 102 represents the REOG of an instrument 10 made according to the method of the present invention. As can be seen in FIG. 18, the present invention instrument provided 20 dB more attenuation than did the hard shell, hollow hearing aid instrument represented by the curve 101. Because of the sharp first directional bend of the wearer's ear canal, the hard shell instrument could not be inserted without modification. The apparatus 10 of the present invention was insertable without modification thereby yielding a tighter seal in the wearer's ear.

Figure 19:
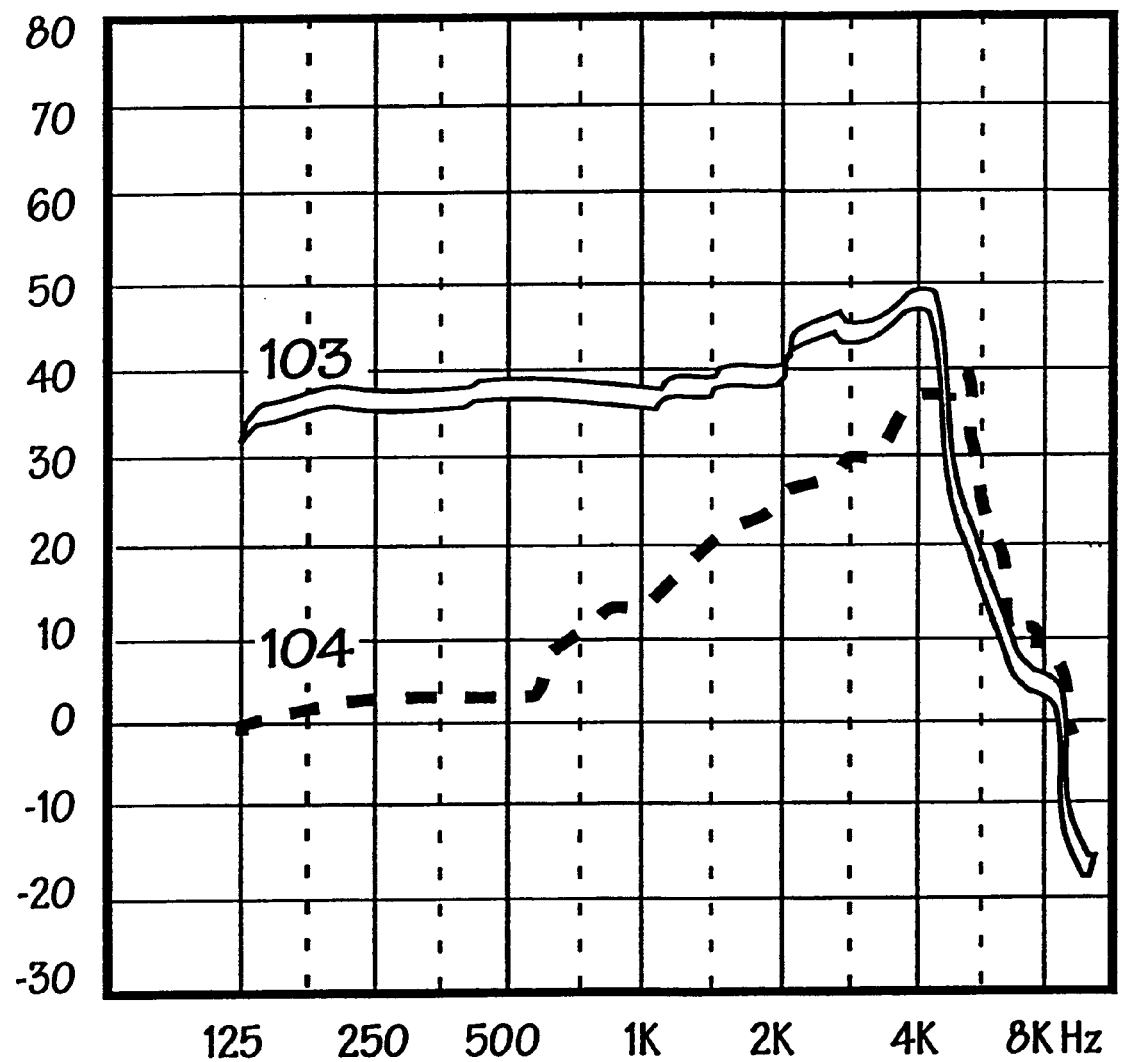
FIG. 19 is a graphical representation showing a comparison of real ear aided gain obtained before acoustic feedback, comparing the present invention with a hard shell, hollow-type instrument.

FIG. 19 is a graphical representation that demonstrates real ear aided gain (REAG) findings obtained from a wearer having a tortuous ear canal. The curves shown (103, 104) were obtained from the instruments used to generate the finding shown in FIG. 18. Curve 103 represent REAG before feedback of the apparatus 10 of the present invention. Curve 104 demonstrates the REAG before feedback of a hard shell, hollow type hearing aid instrument of the prior art. As can be seen in FIG. 19, the instrument 10 of the present invention represented by curve 103 provided more gain across the frequencies. This REAG is inversely proportional to the amount of occlusion gain (REOG) or attenuation provided by the apparatus 10 of the present invention. It should be restated that, because of the sharp first directional bend of the wearer's ear canal, the hard shell, hollow type instrument of the prior art could not be inserted without being modified. The apparatus 10 of the present invention was insertable without modification, thus the present invention provides higher added gain values (REAG) when a more negative REOG can be achieved while maintaining comfort.

Figure 20:
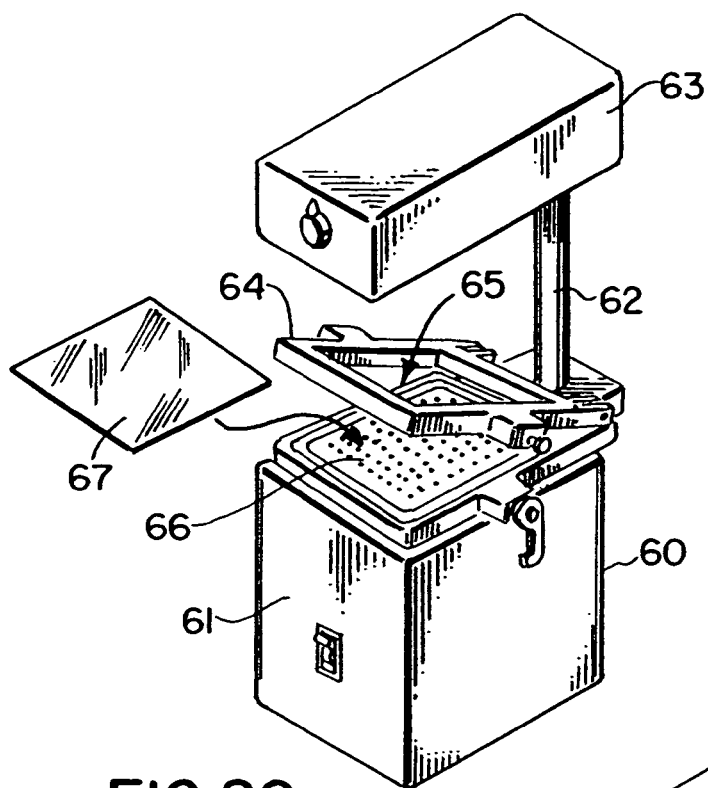
FIG. 20 is a perspective view illustrating an alternate method of the present invention, namely the initial step of forming the female mold.

FIGS. 20–25 show an alternate method for forming the female mold that is then used with the embodiment of FIGS. 1–19. The female mold is designated generally by the numeral 15A in FIG. 26 after forming and using the method steps shown in FIGS. 20–25. In FIG. 20, a vacuum mold apparatus 60 has a base 61 that supports a post 62 and heating element 63. Base 61 contains a vacuum pump. Frame 64 can be pivotally mounted to base 61 at post 62. Frame 64 provides opening 65.

Figure 21:
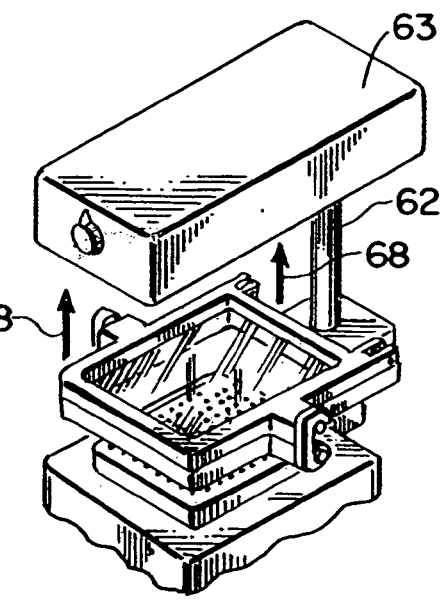
FIGS. 21–22 show the alternate method of the present invention including a heating of the vacuum forming film material.
Figure 22:
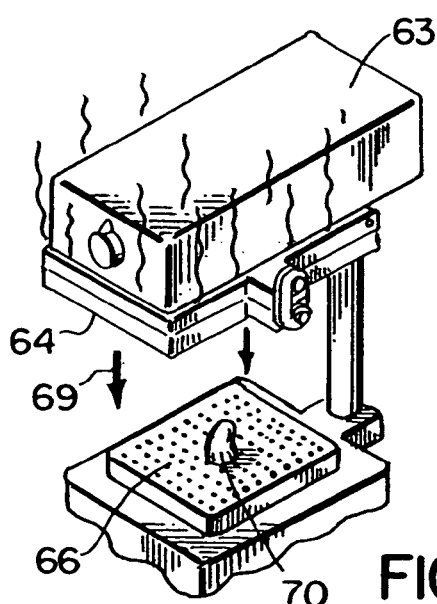

A matrix 66 of small openings is provided at the upper portion of base 61. Matrix 66 of openings communicates with the vacuum pump in base 61. In FIG. 21, the sheet of film material 67 is placed into and raised with frame 64 as indicated by arrows 68 in FIG. 21. In FIG. 22, the sheet of film material 67 is heated by heating element 63 as frame 64 engages or is positioned closely to the heating element 63. Arrows 69 indicate that frame 64 is lowered after heating element 63 heats sheet of film material 67 (FIGS. 22). Male mold 70 is placed upon matrix 66 so that when the heated and softened sheet of film material 67 is lowered with frame 64, the sheet of film material 67 deforms and conforms to the male mold 70 as shown in FIGS. 23 and 24.

Figure 23:
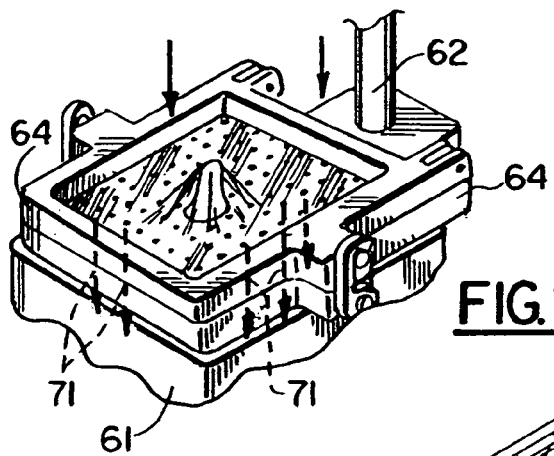
FIG. 23 is a perspective view of the alternate method of the present invention shown during vacuum forming.
Figure 24:
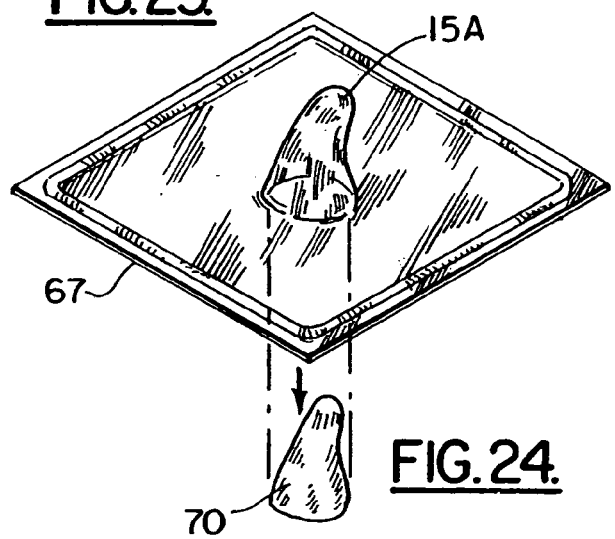
FIG. 24 is a perspective view of the alternate method of the present invention showing the female mold as part of a vacuum formed sheet.
Figure 25:
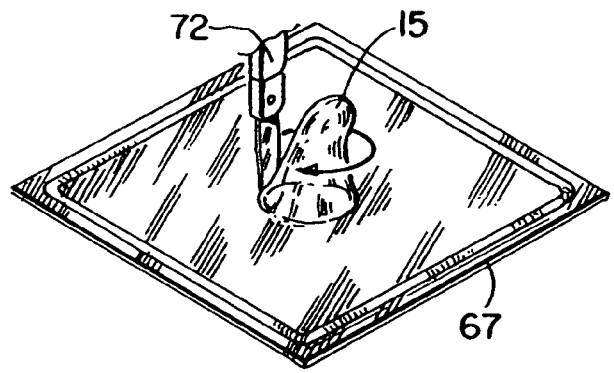
FIG. 25 is a perspective view of the alternate method of the present invention showing removal of the female mold from the vacuum molded sheet.
Figure 26:
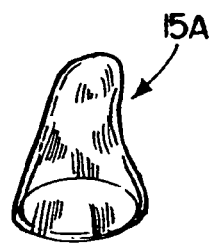
FIG. 26 is a perspective view of the method of the present invention showing the female mold after forming using the method steps of FIGS. 23–25.

A vacuum is drawn through the matrix of opening 66 using the vacuum pump in base 61 as indicated by the arrows 71 in FIG. 23. When the vacuum is discontinued, the male mold 70 is withdrawn, and the female mold 15A is formed as part of sheet 67 as shown in FIGS. 24 and 25. The female mold 15A can then be removed using knife 72. FIG. 26 shows the completed female mold 15A.

It should be understood that the female mold 15A can be used in place of the female mold 15 in the embodiment of FIGS. 1–19 and in the method of FIGS. 1–19.

FIGS. 27–32 show a second alternate embodiment of the apparatus of the present invention, and illustrate the second alternate embodiment of the method of the present invention. In FIGS. 27–32, a second, alternate embodiment of the apparatus of the present invention is shown, designated generally by the numeral 75 in FIGS. 29, 30 and 31. Hearing aid 75 is constructed using the method shown in FIGS. 27–32. In FIG. 27, vent tube 76 is shown prior to attachment to mounting member (e.g. acrylic) 77. The mounting member 77 has an opening 78. It should be understood that the mounting member 77 can receive any of the female molds 15, 15A shown in the embodiments of FIGS. 1–26.

An insert 79 includes several sections designed to simulate portions of a hearing aid component assembly 105. For example, the insert 79 can include a section 80 designed to simulate an electronic hearing aid component, namely a receiver. The insert section 81 is designed to simulate a wiring harness. The insert section 82 is designed to simulate a battery compartment or battery receptacle.

Figure 11:
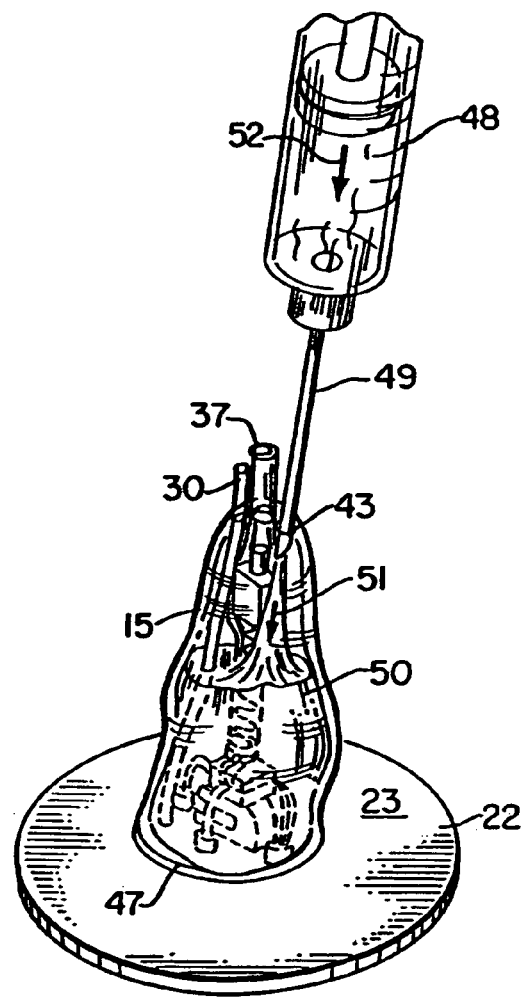
FIG. 11 is a perspective view illustrating the method step of adding filler material to the interior of the female mold and encapsulating electronic hearing aid component portions of the apparatus.

Once the selected mold such as 15, 15A is attached to mounting member 77, it can be filled with a polymeric material (preferably silicone), such as is shown in FIG. 11. However, in the embodiment of FIGS. 27–32, vent tube 76 is first coated with a bonding agent 149 such as A330 available from Factor II of Lakeside, Ariz. The vent tube 76 is then placed inside the mold cavity 15, 15A. The mold 15, 15A is then attached (bonded) to mounting member 77 as shown and described with respect to the embodiments of FIGS. 1–26 (see FIG. 11). Once the polymeric material has cured inside mold cavity, the mold 15, 15A can be removed as indicated schematically by arrow 94. A technician then removes insert 78 as indicated schematically by the arrow 83 in FIG. 28. The insert 79 includes an insert section 80 that simulates a receiver, an insert section 81 that simulates a wiring harness and an insert section 82 that simulates a battery compartment or battery receptacle. However, other shapes can be used for insert 136 so that a cavity 141 of desired shape is achieved. Upon removal of the insert 79, a cavity 84 is left behind, the cavity 84 being positioned next to vent tube 76 as shown in FIG. 28.

The cavity 84 simulates the sections of the provided insert 79, including a cavity section 85 that simulates a receiver, a cavity section 86 that simulates a wiring harness and a cavity section 87 that simulates a battery case or receptacle.

The bonding enhancer 92 can be applied to vent tube 76 using a spray or brush 88 as shown in FIG. 27 as indicated schematically by the arrow 89. Vent tube 76 thus has an outer surface 90 that becomes coated with the bonding enhancer or bonding agent 92. Vent tube 76 provides a bore 91 which is not coated with the bonding enhancer, as it remains open to vent air flow in between the patient's ear canal and the exterior of the ear canal and hearing aid 75.

The polymeric filler material 93 that is added to mold 15, 15A cavity forms a soft and solid body having the provided cavity 84 into which a hearing aid component assembly 105 can be inserted, as indicated schematically by arrows 99 in FIG. 29. This hearing aid component assembly can include both electronic hearing aid components and other components. As an example, in FIG. 29, the hearing aid component assembly 105 includes a receiver 95, receiver tube 96, wiring harness 97, and a battery compartment 98 that includes other hearing aid components such as battery 101, a microphone, an amplifier, or other desired hearing aid components.

FIGS. 29–31 illustrate the completion of and insertion of hearing aid component assembly 105 into the cavity 84 that was formed after the polymeric filler material 93 had cured and set, and after which the shaped insert 79 had been removed. In FIG. 31, arrows 100 schematically indicate a severing of excess vent tube 76 material and the severance of excess material from receiver tube 96. The receiver tube 96 and vent tube 76 communicate with the patient's inner ear generally opposite mounting member 77 as shown in FIGS. 28–31. The vent tube 76 also communicates with the exterior of the patient's ear via an opening 104 in mounting member 77 (see FIG. 32). A connection 103 can be formed between vent tube 76 and mounting member 77 using a needle 102 to apply an adhesive or other connection material or structure, for example.

The apparatus 10 of the present invention will result in a better utilization of advanced circuitry and a more comfortable hearing instrument. The soft construction solves the problem of peripheral leakage, poor fit, and pivotal displacement that often occurs with jaw motion.

Another problem that is solved with the present invention is the elimination of internal cross-talk of components housed in hollow shell type hearing aids.

The following table lists the parts numbers and parts descriptions as used herein and in the drawings attached hereto.

PARTS LIST

Part Number Description
1 ear
2 external auditory canal
3 ear canal wall
4 auricle
5 isthmus
6 tympanic membrane
7 middle ear
8 inner ear
9 dam
10 hearing aid
11 form
12 knife
13 excess material
14 excess material
15 female mold
15A female mold
16 sagittal plane
17 vessel
18 technician's fingers
19 annular surface
20 arrow
21 mold material
22 mounting member
23 medial side
24 lateral side
25 microphone
26 battery compartment
27 volume control
28 programming socket
29 vent opening
30 vent tube
31 battery
32 battery terminal
33 voltage regulating capacitor
34 amplifier/microprocessor
35 receiver
36 receiver port
37 receiver tube
38 wiring harness
39 s-loop wires
40 arrow
41 opening
42 opening
43 opening
44 distal end
45 proximal end
46 dotted line
47 temporary seal
48 syringe
49 needle
50 filler material
51 arrow
52 arrow
53 interior space
54 silicone plug
55 monofilament cantilever
56 opening
57 fastener
58 small opening
59 large opening
60 vacuum mold
61 base
62 post
63 heating element
64 frame
65 opening
66 matrix
67 sheet of film material
68 arrow
69 arrow
70 male mold
71 arrow
72 knife
75 hearing aid
76 vent tube
77 mounting member
78 opening
79 insert
80 insert section
81 insert section
82 insert section
83 arrow
84 cavity
85 cavity section
86 cavity section
87 cavity section
88 brush
89 arrow
90 outer surface
91 bore
92 bonding agent
93 filler material
94 arrow
95 receiver
96 receiver tube
97 wiring harness
98 battery compartment
99 arrow
100 arrow
101 battery
102 needle
103 connection
104 opening
105 hearing aid component assembly The foregoing embodiments are presented by way of example only; the scope of the present invention is to be limited only by the following claims.

The invention claimed is:

1. A method of manufacturing a hearing aid comprising the steps of:
  a) placing a moldable material in the ear canal of a patient to cast a form;
  b) using the form to form a hollow shell with an outer surface that approximates the shape of the patient's ear canal, the shell being of a soft polymeric material;
  c) providing a mounting member;

d) mounting electronic hearing aid components to the mounting member;
e) joining the mounting member to the hollow shell to define a mold cavity;
f) filling the shell with a soft polymeric material that substantially encapsulates at least one of the electronic components and bonds to the mounting member;
g) wherein the combination of shell, electronic components and soft polymeric material define a soft structure that is compliant to ear canal movement during use.

2. The method of claim 1 further comprising the step of eliminating substantially all void space between the shell and the electronic components with the filling in step "f" so that feedback is minimized.

3. The method of claim 1 wherein step "c" comprises providing a mounting member that is a rigid plastic member.

4. The method of claim 1 wherein step "c" comprises providing a mounting member that is an acrylic member.

5. The method of claim 1 wherein in step "c" the mounting member has medial and lateral side portions.

6. The method of claim 5 wherein in step "d" electronic hearing aid components are attached to the medial side portion of the mounting member.

7. The method of claim 1 wherein in step "f" filling includes encapsulating at least a receiver electronic hearing aid component.

8. The method of claim 1 wherein step "f" comprises filling the shell with a soft silicone material that substantially encapsulates at least one of the electronic components.

9. The method of claim 1 further comprising placing a bonding layer between the mounting member and soft polymeric material.

10. The method of claim 1 wherein in step "f" the soft polymeric material has a hardness of between about 3 and 55 Durometer Shore A.

11. A method of manufacturing a hearing aid comprising the steps of:
a) forming a hollow shell with an inside surface that approximates the shape of the human ear canal, the shell being of a soft polymeric material;
b) providing a mounting member;
c) mounting electronic hearing aid components to the mounting member;
d) joining the hollow shell to the mounting member to define a mold cavity;
e) filling the mold cavity with a soft polymeric material that substantially encapsulates the electronic components and bonds to the mounting member;
f) eliminating substantially all void space between the shell and the electronic components with the filling in step "e";
g) allowing the soft polymeric material to cure;
h) wherein the combination of electronic components and soft polymeric material define a soft structure that is compliant to ear canal movement during use.

12. The method of claim 11 further comprising the step of removing the shell.

13. The method of claim 11 further comprising the steps of making an impression of the user's ear canal to construct a form and using the form to shape the inside surface of the hollow shell.

14. The method of claim 11 further comprising the step of using a male mold to form the inside surface of the hollow shell.

15. The method of claim 11 wherein the shell and mounting members are temporarily joined with a seal in step "d".

16. The method of claim 11 wherein in step "e" at least a receiver is encapsulated.

17. The method of claim 11 wherein in step "e" at least a receiver and wiring harness are encapsulated.

18. The method of claim 11 further comprising the step of using a bonding enhancer to join the soft polymeric material to the mounting member.

19. The method of claim 11 wherein in step "b" the mounting member has a hard plastic surface and further comprising the step of using a bonding layer to join the soft polymeric material to the mounting member.

20. The method of claim 19 wherein the bonding layer includes multiple coatings applied to the mounting member.

21. The method of claim 11 wherein in step "b" the mounting member is a hard plastic and in step "e" the soft polymeric material includes silicone.

22. A method of manufacturing a hearing aid comprising the steps of:
a) making a male mold that accurately conforms to the shape of a patient's ear canal;
b) using the male mold to form a female mold with an inside surface that generally duplicates the shape of the male mold and at least a section of the patient's ear canal;
c) providing a mounting member;
d) mounting electronic hearing aid components to the mounting member;
e) attaching the mold to the mounting member to define a cavity;
f) filling the cavity with a soft polymeric material that substantially encapsulates at least one of the electronic components and bonds to the mounting member; and
g) wherein the combination of the shell, soft polymeric material, and electronic component define a soft structure that is compliant to ear canal movement during use.

23. The method of claim 22, wherein the hearing aid is sized to fit completely in the ear canal of the patient.

24. The method of claim 1, wherein the hearing aid is sized to fit completely in the ear canal of the patient.

25. The method of claim 11, wherein the hearing aid is sized to fit completely in the ear canal of the patient.

26. A method of manufacturing a hearing aid comprising the steps of:
a) providing a mounting member with at least one opening;
b) using a form to form a hollow shell with an outer surface that approximates the shape of a patient's ear;
c) joining the mounting member to the hollow mold having a mold cavity;
d) placing a vent tube inside the mold cavity;
e) placing an insert inside the mold cavity, the insert having a configuration that generally simulates a hearing aid component assembly;
f) filling the shell with a soft polymeric material that sets to form a soft-solid structure that substantially encapsulates the vent tube and the insert and bonds to the mounting member;
g) removing the insert from the soft, solid structure to form a void space; and
h) placing a hearing aid component assembly into the void space.

27. The method of claim 26 further comprising the step of eliminating substantially all void space between the mold and the hearing aid components with the filling step so that feedback is minimized.

28. The method of claim 26 wherein step "a" comprises providing a mounting member that is a rigid plastic member.

29. The method of claim 26 wherein step "a" comprises providing a mounting member that is an acrylic member.

30. The method of claim 26 wherein in step "a" the mounting member has medial and lateral side portions.

31. The method of claim 30 wherein the electronic hearing aid components are attached to the medial side portion of the mounting member.

32. The method of claim 26 wherein the hearing aid components assembly includes at least one receiver and filling includes encapsulating at least a receiver simulated insert section.

33. The method of claim 26 wherein step "f" comprises filling the shell with a soft silicone material.

34. The method of claim 26 further comprising placing a bonding layer between the mounting member and soft polymeric material.

35. The method of claim 1 further comprising placing a bonding material on the vent tube.

36. The method of claim 26 wherein in step "f" the soft polymeric material has a hardness of between about 3 and 40 Durometer Shore A.

37. A method of manufacturing a hearing aid comprising the steps of:
  a) forming a hollow shell with an inside surface that approximates the shape of the human ear canal;
  b) providing a mounting member;
  c) joining the hollow shell to the mounting member to define a mold cavity;
  d) placing a vent tube and an insert inside the mold cavity;
  e) coating the vent tube with a bonding agent;
  f) filling the mold cavity with a soft polymeric material that substantially encapsulates the vent tube and insert;
  g) eliminating substantially all void space between the shell and the components with the filling in step "g";
  h) allowing the soft polymeric material to cure;
  i) removing the insert to leave a void space inside the soft polymeric material;
  j) placing a hearing aid component assembly inside the void space;
  k) wherein the combination of components and soft polymeric material define a soft structure that is compliant to ear canal movement during use.

38. The method of claim 36 further comprising the step of removing the shell.

39. The method of claim 36 further comprising the steps of making an impression of the user's ear canal to construct a form and using the form to shape the inside surface of the hollow shell.

40. The method of claim 36 further comprising the step of using a male mold to form the inside surface of the hollow shell.

41. The method of claim 36 wherein the shell and mounting members are temporarily joined with a seal in step "c".

42. The method of claim 36 wherein in step "f" at least a receiver shaped insert section is encapsulated.

43. The method of claim 36 wherein in step "f" at least receiver and wiring harness shaped insert sections are encapsulated.

44. The method of claim 36 wherein in step "f" at least receiver, wiring harness and battery compartment shaped insert sections are encapsulated.

45. The method of claim 36 further comprising the step of using a bonding enhancer to join the soft polymeric material to the mounting member.

46. The method of claim 36 wherein in step "b" the mounting member has a hard plastic surface and further comprising the step of using a bonding layer to join the soft polymeric material to the mounting member.

47. The method of claim 44 wherein the bonding layer includes multiple coatings applied to the mounting member.

48. The method of claim 36 wherein in step "b" the mounting member is a hard plastic and in step "f" the soft polymeric material includes silicone.

49. A method of manufacturing a hearing aid comprising the steps of:
  a) making a mold with an inside surface that generally duplicates the shape of and at least a section of a patient's ear canal;
  b) attaching the mold to a mounting member to define a mold cavity;
  c) placing a vent tube and an insert inside the mold cavity;
  d) filling the mold cavity with a soft polymeric material that substantially encapsulates the vent tube and the insert;
  e) removing the insert after the material cures to leave a void space;
  f) placing a hearing aid component assembly insert into the void space;
  g) wherein the combination of shell soft polymeric material and hearing aid component assembly define a soft structure that is compliant to ear canal movement during use.

50. The method of claim 49, wherein the hearing aid is sized to fit completely in the ear canal of the patient.

51. The method of claim 26, wherein the hearing aid is sized to fit completely in the ear canal of the patient.

52. The method of claim 37, wherein the hearing aid is sized to fit completely in the ear canal of the patient.

* * * * *